US011083761B2

(12) United States Patent
Parks et al.

(10) Patent No.: US 11,083,761 B2
(45) Date of Patent: Aug. 10, 2021

(54) **HIGH POTENCY STABLE FORMULATIONS OF VAGINAL *LACTOBACILLUS***

(71) Applicant: Osel, Inc., Mountain View, CA (US)

(72) Inventors: Thomas P. Parks, San Mateo, CA (US); Angela Marcobal, Mountain View, CA (US)

(73) Assignee: Osel, Inc., Mountain View, CA (US)

( * ) Notice: Subject to any disclaimer, the term of this patent is extended or adjusted under 35 U.S.C. 154(b) by 0 days.

(21) Appl. No.: 16/825,225

(22) Filed: Mar. 20, 2020

(65) Prior Publication Data

US 2020/0230183 A1 Jul. 23, 2020

Related U.S. Application Data

(63) Continuation of application No. 16/627,118, filed as application No. PCT/US2018/040884 on Jul. 5, 2018, now abandoned.

(60) Provisional application No. 62/529,756, filed on Jul. 7, 2017.

(51) Int. Cl.

| | |
|---|---|
| ***A61K 35/747*** | (2015.01) |
| ***A61P 15/02*** | (2006.01) |
| ***A61P 31/04*** | (2006.01) |
| ***A61K 9/00*** | (2006.01) |
| ***A61K 9/19*** | (2006.01) |
| ***A61K 45/06*** | (2006.01) |
| ***A61K 47/02*** | (2006.01) |
| ***A61K 47/10*** | (2017.01) |
| ***A61K 47/18*** | (2017.01) |
| ***A61K 47/22*** | (2006.01) |
| ***A61K 47/26*** | (2006.01) |
| ***C12N 1/04*** | (2006.01) |
| ***C12N 1/20*** | (2006.01) |
| ***A61K 35/00*** | (2006.01) |

(52) U.S. Cl.

CPC .......... *A61K 35/747* (2013.01); *A61K 9/0034* (2013.01); *A61K 9/19* (2013.01); *A61K 45/06* (2013.01); *A61K 47/02* (2013.01); *A61K 47/10* (2013.01); *A61K 47/183* (2013.01); *A61K 47/22* (2013.01); *A61K 47/26* (2013.01); *A61P 15/02* (2018.01); *A61P 31/04* (2018.01); *C12N 1/04* (2013.01); *C12N 1/20* (2013.01); *A61K 2035/115* (2013.01)

(58) Field of Classification Search

CPC .......... A61P 31/04; A61P 15/02; A61K 47/22; A61K 45/06; A61K 9/19; A61K 47/10; A61K 47/183; A61K 35/747; A61K 47/02; A61K 47/26; A61K 9/10; A61K 9/0034; A61K 2035/115; C12N 1/20; C12N 1/04

See application file for complete search history.

(56) References Cited

U.S. PATENT DOCUMENTS

| | | | | |
|---|---|---|---|---|
| 2,463,768 | A * | 3/1949 | Hepp | C07C 2/60 585/727 |
| 6,200,609 | B1 * | 3/2001 | Meister | A23C 11/106 426/61 |
| 2002/0090365 | A1 | 7/2002 | Chrisope | |
| 2010/0151026 | A1 | 6/2010 | Liu et al. | |
| 2011/0066137 | A1 | 3/2011 | Parks et al. | |
| 2014/0199281 | A1 * | 7/2014 | Henn | A61K 38/13 424/93.46 |
| 2017/0020934 | A1 | 1/2017 | Liu | |

FOREIGN PATENT DOCUMENTS

| | | | |
|---|---|---|---|
| CN | 102757922 | A | 10/2012 |
| EP | 3040413 | A1 | 7/2016 |
| WO | 9846261 | A1 | 10/1998 |
| WO | 2014106541 | A1 | 7/2014 |

OTHER PUBLICATIONS

Dolly et al. "Microencapsulation of Lactobacillus Plantarum (mtcc 5422) by Spray-Freeze-Drying Method and Evaluation of Survival in Simulated Gastrointestinal Conditions", Journal of Microencapsulation, 2011, 28(6):568-574.
PCT/US2018/040884, "International Prelimiary Report on Patentability", dated Jan. 16, 2020, 11 pages.
PCT/US2013/040884 , "International Search Report and Written Opinion", dated Sep. 13, 2018, 12 pages.
Whaley et al., "Novel Approaches to Vaginal Delivery and Safety of Microbicides: Biopharmaceuticals, Nanoparticles, and Vaccines", Antiviral Research, Elsevier B.V., vol. 88, Dec. 1, 2010, pp. 55-66.
EP18827562.2 , "Extended European Search Report", dated Apr. 7, 2021, 11 pages.

* cited by examiner

*Primary Examiner* — Sean C. Barron
(74) *Attorney, Agent, or Firm* — Kilpatrick Townsend & Stockton LLP

(57) ABSTRACT

This invention provides for a dry preserved formulation of *Lactobacillus* suitable for administration to people as a pro-biotic or live biotherapeutic treatment where the formulation is stable, has high potency, and contains no animal-derived excipients.

18 Claims, 2 Drawing Sheets

HIGH POTENCY STABLE FORMULATIONS OF VAGINAL *LACTOBACILLUS*

CROSS-REFERENCES TO RELATED APPLICATIONS

The present application is a Continuation of U.S. patent application Ser. No. 16/627,118, filed on Dec. 27, 2019, which is a U.S. National Phase of PCT/US2018/040884, filed on Jul. 5, 2018, which claims priority to U.S. Provisional Patent Application No. 62/529,756, filed on Jul. 7, 2017, the contents of all of the above are incorporated in their entireties herein for all purposes.

BACKGROUND OF THE INVENTION

The mucosal membranes of all humans are naturally colonized by bacterial microbiota. Recent studies have indicated that the microbiota found in the human gut, mouth and vagina, interact closely with cells and tissues of the body to regulate natural biological processes such as non-specific host defense. See, e.g., Redondo-Lopez, et al. (1990) *Rev. Infect. Dis.* 12:856-872; Gilbert, J. A., et al. *Nature* 2016 Jul. 7, 535(7610):94-103; McDermott, A. J., et al. *Immunology* 2014 May, 142(1):24-31; Nelson, D. B., et al. *Anaerobe* 2016 December, 42:67-73. Generally, healthy vaginal microbiota is dominated by *Lactobacillus* species, which are gram positive rods that play an important role in resisting infection via production of lactic acid and acidification of the vagina, or by production of other antimicrobial products, such as hydrogen peroxide ($H_2O_2$). The species of *Lactobacillus* most commonly isolated from the reproductive tracts of healthy women worldwide include *L. crispatus, L. jensenii, L. gasseri*, and *L. iners*. See, e.g., Antonio et al., (1999) *J. Infect. Dis.* 180:1950-1956; Vasquez et al., (2002) *J. Clin. Microbiol.* 40:2746-2749; Vallor, A. C., et al. *J Infect Dis.* 2001 Dec. 1, 184(141431-6; Ravel, J., et al. *Proc Natl Acad Sci, USA.* 2011 Mar. 15, 108 Suppl 1:4680-7. *L. crispatus, L. jensenii*, and *L. gasseri* are capable of producing $H_2O_2$, whereas *L. iners* strains generally do not produce $H_2O_2$. These species are phylogenetically and functionally different from food and/or environmental *Lactobacillus* species. These facultative anaerobes metabolize glucose to lactic acid, contributing to the maintenance of a low vaginal pH (4.0-4.5) that accounts for a major part of the non-specific host defense of the vagina. An acidic pH has a significant antagonistic effect on the growth of opportunistic commensal and pathogenic organisms, and, lactic acid has antiviral activity against HIV and HSV-2.

The $H_2O_2$-producing strains (e.g. *L. crispatus* and *L. jensenii*) are more protective than those that do not produce $H_2O_2$ (*L. iners*). Indeed, it has been demonstrated that women with vaginal mucosa colonized with sufficient amounts of protective *Lactobacillus* spp. have a 50% lower frequency of gonorrhea, chlamydial infections, trichomoniasis and bacterial vaginosis. The presence of $H_2O_2$-producing lactobacilli in the vagina have been linked to a decreased frequency of bacterial vaginosis, symptomatic yeast vaginitis and sexually transmitted pathogens including *Neisseria gonorrhea, Chlamydia trachomatis*, and *Trichomonas vaginalis*. In vitro studies have demonstrated that $H_2O_2$-producing lactobacilli have potent bactericidal and viricidal properties against vaginal pathogens, including human immunodeficiency virus (HIV). Therefore, beneficial lactobacilli associated with the vaginal mucosa can be considered to provide a protective “biofilm”. See e.g., Falagas et al., (2006) *Drugs,* 66:1253-1261.

Many vaginal and systemic medications may kill vaginal *Lactobacillus*, and the depletion of the dominant vaginal *Lactobacillus* species leads to a more diverse abnormal microbiota populated with facultative and strict anaerobes, such as *Gardnerella vaginalis* and *Atopobium vaginae*, higher vaginal pH, and higher levels of proinflammatory cytokines, which can be associated with the development of clinical syndromes, such as bacterial vaginosis (BV), establishment of opportunistic infections, and an increased risk of acquiring HIV-1 and Herpes simplex virus type 2 (HSV-2) in women. See, e.g., Sha et al. (2005) *J. Infect. Dis.* 191:25-32; Taha et al. (1998) *AIDS* 12:1699-1706; Bolton, M., et al. *Sex Trans Dis* 2008 March 35(3):214-215. Hence, treatment of sexually transmitted diseases with antibiotics may place women at increased risk for repeated acquisition of the diseases. These findings, along with the widespread belief that lactobacilli generally promote vaginal health, have suggested to clinicians that women should recolonize the vagina with *Lactobacillus* to prevent or treat urogenital tract infections.

There has been considerable interest in the development of non-antibiotic, ecologically appropriate approaches, such as *Lactobacillus* Replacement Therapy (LRT) to replenish the healthy vaginal microbiota and to prevent urogenital infections. The success of LRT depends in part on selection of an ecologically appropriate *Lactobacillus* strain, cell preservation, recovery of the dry *Lactobacillus* formulation following rehydration, as well as the extent and duration of vaginal colonization. Various methods for administering beneficial bacteria and other substances to the vaginal mucosa are known. In fact, *Lactobacillus* products for intravaginal or oral use have been available for over 100 years in the form of “*acidophilus*” preparations available in health food stores, and *acidophilus* milk or yogurt bought in grocery stores (e.g., these products typically advertise the inclusion of a strain of *Lactobacillus acidophilus*). These products have included vaginal tablets, capsules, and vaginal suppositories containing lyophilized *Lactobacillus acidophilus* of human origin as well as various nutritional supplements.

These products are largely non-efficacious due to the failure of the products to colonize the vagina with the exogenous lactobacilli. These failures are often due to the poor quality of the commercially available products and that *Lactobacillus* species contained in probiotics are not of vaginal origin, and thus are not appropriate for the vagina. It has been documented that *Lactobacillus* products sold as foods or as *Lactobacillus* supplements are often contaminated with other potential pathogens. In addition, *Lactobacillus* obtained from yogurt are unable to bind to vaginal epithelial cells. The binding of lactobacilli to the epithelial cells is a necessary step to establish colonization of the host organism. Furthermore, the low percentage of physiologically viable cells reflected by the low recovery in simulated vaginal fluid significantly affects the actual bacterial dosage.

Therefore, a product is needed for the treatment of vaginal infections, which can be manufactured under exacting conditions and which uses appropriate human strains of *Lactobacillus* having in vivo microbicidal properties, adherence to vaginal epithelial cells, and an effective potency of viable microbes. The present invention addresses these and other needs.

BRIEF SUMMARY OF THE INVENTION

In one aspect, the present invention provides for an aqueous bacterial suspension of vaginal *Lactobacillus* species, which has no animal-derived excipients. The suspension can result from a combination of a cell pellet of vaginal *Lactobacillus* species and an aqueous preservation medium. The aqueous preservation medium can be comprised of trehalose at between 5-20% (w/v), xylitol at between 2-9% (w/v), sodium ascorbate at between 0.5-1.5% (w/v), sodium phosphate at between 10-50 mM, and, optionally, sodium glutamate at between 0-5% (w/v).

In another aspect, the present invention provides for a method of preserving *Lactobacillus* spp. under dry conditions, in the absence of animal-derived excipients. The method involves obtaining an aqueous suspension of a vaginal *Lactobacillus* species having a cell concentration between about $10^8$ to about $10^{10}$ per ml, centrifuging the solution to form a bacterial cell pellet, and resuspending the bacterial cell pellet in an aqueous preservation medium. The aqueous preservation medium can be comprised of trehalose at between 5-20% (w/v), xylitol at between 2-9% (w/v), sodium ascorbate at between 0.5-1.5% (w/v), sodium phosphate at between 10-50 mM, and, optionally, sodium glutamate at between 0-5% (w/v). The resulting bacterial suspension can have a weight ratio of the cell pellet wet weight (i.e., grams of cell pellet following centrifugation and decanting the supernatant) to preservation media (ml) of between 1:1 and 1:5 grams of pellet to milliliter of preservation media.

Another aspect of the present invention provides a method of treating abnormal vaginal microbiota in women. The method involves selecting a woman having a diagnosis of abnormal vaginal microbiota, administering an antibiotic in an amount effective to reduce the level of abnormal vaginal microbiota, followed by the administration of a dry powder derived from an aqueous bacterial suspension of vaginal *Lactobacillus* species with no animal-derived excipients. The aqueous suspension is the result of a combination of a cell pellet of vaginal *Lactobacillus* species with an aqueous preservation medium, which can be comprised of trehalose at between 5-20% (w/v), xylitol at between 2-9% (w/v), sodium ascorbate at between 0.5-1.5% (w/v), sodium phosphate at between 10-50 mM, and, optionally, sodium glutamate at between 0-5% (w/v).

In some embodiments, the method of treating abnormal vaginal microbiota in a woman involves the daily administration of an antibiotic for between 2 and 7 days and the administration of the dry powder can begin at any time between two days before the cessation of the administration of an antibiotic and two days after the administration of an antibiotic. In some cases, the antibiotic can be clindamycin, metronidazole or tinidazole.

The following embodiments can be combined with any of the above aspects of the invention. For example, in some embodiments, the vaginal *Lactobacillus* species of the aqueous bacterial suspension can produce greater than 0.5 ppm of hydrogen peroxide under effective culture conditions. In other embodiments, the vaginal *Lactobacillus* species can be selected from the species consisting of *Lactobacillus crispatus, Lactobacillus jensenii*, and *Lactobacillus gasseri*.

In some embodiments of the invention, the aqueous preservation medium can be comprised of trehalose at between 5-15% (w/v), xylitol at between 2-7% (w/v), sodium ascorbate at between 0.5-1.0% (w/v), sodium phosphate at between 10-30 mM, and, optionally, sodium glutamate at between 0-5% (w/v).

In another embodiment, the bacterial suspension can be lyophilized to yield a dry powder. The dry powder can have a water activity value of less than 0.220. In some embodiments, the powder can be combined with an inactive excipient at a ratio of powder:excipient of between 1:1 and 1:10 w/w to adjust the concentration of colony forming units. Alternatively, the dry bacterial powder can be combined with an excipient blend to adjust the potency of the final product. For convenience, the dry powder can be contained within a plastic housing designed for vaginal administration.

In some embodiments of the invention, the aqueous preservation medium of the bacterial suspension does not contain skim milk. In another embodiment, the aqueous preservation medium of the bacterial suspension does not contain α-tocopherol. In some embodiments of the invention, the aqueous preservation medium of the bacterial suspension does not contain skim milk or α-tocopherol.

In some embodiments of the invention, the aqueous preservation medium can be comprised of trehalose at between 5-20% (w/v), xylitol at between 2-9% (w/v), sodium ascorbate at between 0.5-1.5% (w/v), sodium phosphate at between 10-50 mM, and, optionally, sodium glutamate at between 0-5% (w/v), wherein the aqueous preservation medium does not contain skim milk. In some embodiments of the invention, the aqueous preservation medium can be comprised of trehalose at between 5-20% (w/v), xylitol at between 2-9% (w/v), sodium ascorbate at between 0.5-1.5% (w/v), sodium phosphate at between 10-50 mM, and, optionally, sodium glutamate at between 0-5% (w/v), wherein the aqueous preservation medium does not contain α-tocopherol. In some embodiments of the invention, the aqueous preservation medium can be comprised of trehalose at between 5-20% (w/v), xylitol at between 2-9% (w/v), sodium ascorbate at between 0.5-1.5% (w/v), sodium phosphate at between 10-50 mM, and, optionally, sodium glutamate at between 0-5% (w/v), wherein the aqueous preservation medium does not contain skim milk or α-tocopherol.

In an aspect, the invention relates to a composition comprising a dry powder derived from an aqueous bacterial suspension of vaginal *Lactobacillus* species with no animal-derived excipients for use in the treatment of a woman having a diagnosis of abnormal vaginal microbiota, wherein said woman has previously been treated with an antibiotic in an amount effective to reduce the level of abnormal vaginal microbiota; and wherein said aqueous bacterial suspension results from a combination of a cell pellet of vaginal *Lactobacillus* species with an aqueous preservation medium consisting essentially of: (a) trehalose at between 5-20%, w/v; (b) xylitol at between 2-9%, w/v; (c) sodium ascorbate 0.5-1.5%, w/v; and (d) sodium phosphate at between 10-50 mM. In some embodiments, the aqueous preservation medium optionally comprises sodium glutamate at between 0-5%.

Another aspect of the invention relates to a kit of parts for use in the treatment of a woman having a diagnosis of abnormal vaginal microbiota, said kit of parts comprising: a first container comprising one or more antibiotics in an amount effective to reduce the level of abnormal vaginal microbiota; a second container comprising an amount of a composition comprising a dry powder derived from an aqueous bacterial suspension of vaginal *Lactobacillus* species with no animal-derived excipients where the suspension results from a combination of a cell pellet of vaginal *Lactobacillus* species with an aqueous preservation medium consisting essentially of: (a) trehalose at between 5-20%, w/v; (b) xylitol at between 2-9%, w/v; (c) sodium ascorbate 0.5-1.5%, w/v; and (d) sodium phosphate at between 10-50 mM; and optionally, instructions for use of said kit in the treatment of a woman having a diagnosis of abnormal vaginal microbiota. In some embodiments, the aqueous preservation medium optionally comprises sodium glutamate at between 0-5%.

In an embodiment, said one or more antibiotics are for administration for e.g. between 2 and 7 days to said woman; and wherein said dry powder is for administration at any time between two days before the completion of antibiotic administration and two days after the administration of antibiotic ends.

Thus, the kit of parts is preferably intended for sequential administration of i) the one or more antibiotics followed by ii) the composition comprising a dry powder derived from an aqueous bacterial suspension of vaginal *Lactobacillus* species with no animal-derived excipients, for use in the treatment of a woman having a diagnosis of abnormal vaginal microbiota.

In an embodiment, said vaginal *Lactobacillus* species has the ability to produce greater than 0.5 ppm of hydrogen peroxide under effective culture conditions, wherein the *Lactobacillus* species is e.g. selected from a group of species consisting of: *Lactobacillus crispatus, Lactobacillus jensenii* and *Lactobacillus gasseri.*

It should be noted that embodiments and features described in the context of one of the aspects of the present invention also apply to the other aspects of the invention.

DETAILED DESCRIPTION OF THE INVENTION

I. Introduction

Figure 1:
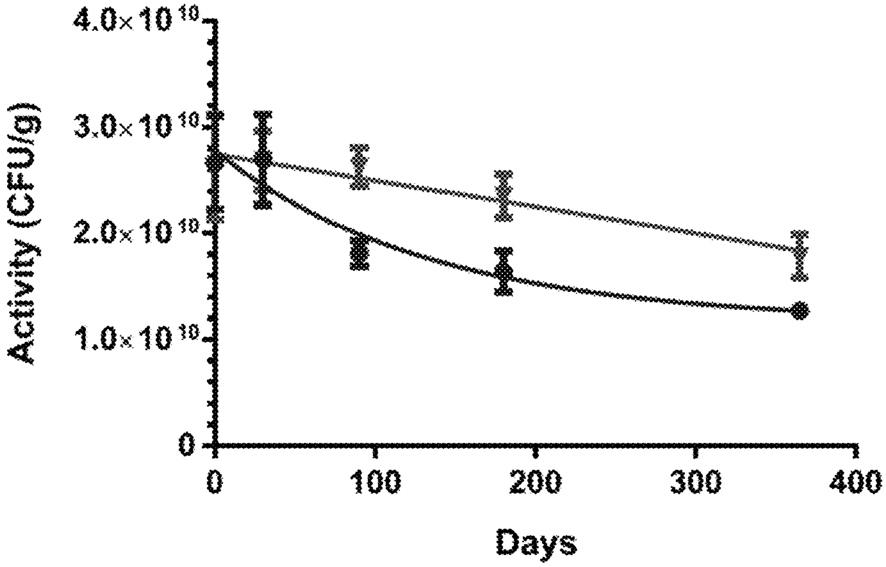
FIG. 1. Stability of LACTIN-V formulated with skim milk (lower line, circles) or without skim milk (upper line, inverted triangles). Powder samples were stored at 25° C. for one year and activity determined at different time points by culturing on MRS agar plates and counting colonies.

This invention provides for a high potency, stable dry preserved formulation of *Lactobacillus* suitable for administration to people as a treatment where the formulation has high colonization potency and no animal-derived excipients. Specifically, as disclosed herein, the present invention provides methods and compositions for *Lactobacillus* Replacement Therapy (LRT) to repopulate the vaginal mucosa with protective *Lactobacillus* microbiota as a means to correct dysbiosis and maintain vaginal health. As described in more detail below, the present invention teaches methods, compositions, and reagents for the preparation and use of transiently buffered dried *Lactobacillus* formulations.

II. Definitions

As used herein, the terms "vaginal microbiota" or "vaginal microbiome" are used interchangeably and refer to the microorganisms that colonize the vagina, although "microbiota" and "microbiome" are the preferred terms. The terms "abnormal vaginal microbiota" or "abnormal vaginal microbiome" or "vaginal dysbiosis" refer to a condition in which the vaginal mucosa lacks protective *Lactobacillus* spp, and is colonized by significant numbers of diverse non-*lactobacillus* spp. The condition can be symptomatic or asymptomatic.

As used herein, the terms "aqueous preservation medium" or "preservation formulation" or "preservation medium" are used interchangeably and refer to a composition capable of preserving and maintaining a bacterial cell culture in a metabolically inactive state while minimizing the damaging effects encountered during the preservation process. Generally, a *Lactobacillus* strain is converted from an actively growing metabolic state to a metabolically inactive state upon addition to the preservation medium, freezing and lyophilization. The preservation medium can therefore be formulated for optimal cell resilience, such that the cells can adhere to mucosal surfaces upon rehydration and return to full metabolic activity. The aqueous preservation medium as used herein is an aqueous solution which typically includes a carbohydrate, a polyol (sugar alcohol), an anti-oxidant, a buffering agent, and, optionally, an amino acid. The aqueous preservation medium is used to resuspend a cell pellet of bacteria to a concentration of about $10^8$ CFU/mL, where the suspension can be dried, stored for at least 2 years at 2-8° C., and resuspended with a loss of CFU of less than 15%.

As used herein, the term "animal-derived excipients" refers to inert substances derived from an animal, which may be included in a composition comprised of substances that are considered active ingredients. Non-limiting examples include milk, yogurt, butter oil, chicken fat, lard, gelatin, and tallow.

As used herein, the term "excipient" and "inactive excipient" are used interchangeably and refer to inert substances formulated alongside the active ingredient of a medication, included for the purpose of long-term stabilization, providing bulk to the powder formulation (thus often referred to as "bulking agents," "fillers," or "diluents"), or to confer a therapeutic enhancement on the active ingredient in the final dosage form, such as facilitating drug absorption, reducing viscosity, or enhancing solubility. Examples of excipients include, without limitation, maltodextrin, starch, pre-gelatinized starch, microcrystalline cellulose, calcium carbonate, dicalcium phosphate, colloidal $SiO_2$, Pharmasperse®, mannitol, trehalose, lactose, sucrose, polyvinyl pyrrolidone, crosspovidone, glycine, magnesium stearate, sodium stearyl fumarate, cyclodextrins and derivatives and mixtures thereof.

As used herein, the term "consisting essentially of" refers to a composition or method that includes the disclosed components or steps, and any other components or steps that do not materially affect the basic and novel characteristics of the compositions or methods. Compositions that consist essentially of listed ingredients do not contain additional ingredients that would affect the essential properties of those bacterial compositions. For example, a *Lactobacillus* powder formulation of the present invention can also be comprised of a pharmaceutically acceptable excipient, such as a coloring agent and/or a filler, and an antiviral or antibacterial agent, and/or an enzyme, without the viability properties of the dry *Lactobacillus* powder being affected.

As used herein, the term "*Lactobacillus*" refers to bacteria that are Gram-positive facultative anaerobic bacteria, characterized by the ability to produce lactate (lactic acid) from carbohydrate sources such as glucose. These bacteria may be present in food products or be commensal organisms that colonize the vaginal or gastrointestinal mucosa.

As used herein, the terms "*Lactobacillus crispatus*" or "*L. crispatus*" refer to a species of the *Lactobacillus* genus. The species is generally distinguished from other lactobacilli based on the polynucleotide sequence of the ribosomal 16S ribosomal RNA gene. "*Lactobacillus gasseri*" or "*L. gasseri*" and "*Lactobacillus jensenii*" or "*L. jensenii*" refer to other species of *Lactobacillus*. *L. crispatus, L. gasseri, L. jensenii* are vaginal species capable of producing hydrogen peroxide.

As used herein, the term "dry composition" refers to a composition from which moisture has been removed. Drying or desiccation techniques include, e.g., heating (e.g., sublimation), application of low pressure or vacuum, lyophilization (i.e., freeze drying), and combinations thereof. Compositions are commonly desiccated for easy storage and transport.

As used herein, the term "effective culture conditions" refers to the environment in which *Lactobacillus* cells are placed in or are exposed to in order to promote growth of said cells. Thus, the term refers to the medium, temperature, atmospheric conditions, substrate, stirring conditions and the like which may affect the growth of cells permitting a generation time (doubling rate of cell population) of about 0.5 to 2.5 hours.

As used herein, the term "potency" refers to the number of viable microbial cells delivered per medicant unit (i.e., medical powder). According to the present invention, viable cells can grow and reproduce. For a *Lactobacillus* dry powder to be efficacious in vivo, both colonization of the vaginal epithelial cells by the microbial cells at a potency of at least about $10^8$ CFU per medicant unit and biological effect (e.g., as evidenced by absence of an infected state such as bacterial vaginosis) are necessary. "High potency" refers to the vaginal medicant containing at least $10^8$ viable microbial cells (CFUs) per medicant unit.

As used herein, the term "lyophilization" refers to the process of freezing a substance and then reducing the concentration of water, by sublimation and/or evaporation to levels which do not support biological or chemical reactions.

As used herein, the term "water activity" and the notation "$a_w$" refer to and are defined to be equal to the Equilibrium Relative Humidity ("ERH") divided by 100. ERH is the equilibrium state at which the dry powder neither absorbs nor loses moisture to the environment. The ERH is influenced by the composition of all ingredients, particularly those with high water contents, which may be present as free or bound water. The amount of free water can influence the storage stability and purity of the dry powder which could result in undesired degradation of activity or growth of contaminating microorganisms during storage.

As used herein, the term "wet weight" refers to the weight (grams) of the cell pellet following centrifugation and decantation of the supernatant. In general, following the step of cell harvesting, centrifuge bottles are pre-weighed, cells are spun down, the supernatant is decanted, and the bottles are weighed again. The difference in weight is the wet weight of the pellet.

III. Compositions and Methods

Obtaining Vaginal Bacteria

A *Lactobacillus* strain suitable for use in a medicant of the present invention (i.e. medical powder) can be any *Lactobacillus* strain that has the identifying characteristics described herein. *Lactobacillus* strains can be detected and isolated from natural sources using appropriate screening techniques that are known in the art. Specifically, suitable strains of *Lactobacillus* for use in a medicant of the present invention can be obtained through publicly available resources, such as American Type Culture Collection (ATCC) or Biodefense and Emerging Infections Research Resources Repository (BEI, beiresources.org) or isolated from the healthy vagina of a human. The identifying characteristics of *Lactobacillus* strains suitable for use in the present invention and methods to screen for these characteristics are discussed in detail below.

One identifying characteristic of a *Lactobacillus* suitable for use in the present invention is that the *Lactobacillus* strain has a percent vaginal epithelial cell (VEC) cohesion value of at least about 50%. A "percent VEC cohesion value" is defined as the percentage of VECs to which at least one *Lactobacillus* cell is adhered in the total number of VECs in an identified group. According to the present invention, the terms "cohesion" and "adherence" can be used interchangeably. Adherence of microbial cells to vaginal epithelial cells is critical for colonization and biological effect. Successful adherence of a *Lactobacillus* cell of the medical powder to a vaginal epithelial cell results in successful colonization of the vaginal epithelial cell. Long term in vivo colonization is a goal of the products and methods of the present invention, and "percent VEC cohesion value" is a good predictor of whether a significant number of VECs will accept microbial cells in vitro and in vivo. Methods used to determine acceptable VEC cohesion values are well known in the art and can be found in U.S. Pat. Nos. 6,468,526 and 6,093,394. See also Kwok, et al., *J. Urol.* 2006, 176:2050-2054.

Another identifying characteristic of a *Lactobacillus* which is suitable for use in a medicant of the present invention is the ability to produce hydrogen peroxide ($H_2O_2$). The $H_2O_2$ positive phenotype is also associated with sustained vaginal colonization. See, e.g., Vallor, A. C., et al., *J Infect Dis.* 2001 Dec. 1; 184(11):1431-6. As discussed above, hydrogen peroxide has been shown to be responsible for the killing of other microorganisms by the *Lactobacillus*. Preferably, the *Lactobacillus* can produce greater than about 0.5 ppm of $H_2O_2$ under normal growth conditions. More preferably, the *Lactobacillus* can produce at least about 10 ppm of $H_2O_2$, and even more preferably, the *Lactobacillus* can produce at least about 20 ppm of $H_2O_2$ under effective growth conditions, herein defined as any medium and conditions capable of promoting production of $H_2O_2$. Effective growth conditions include both in vitro growth conditions (e.g., an effective culture medium and conditions) and in vivo growth conditions (e.g., successful colonization of the vagina). Hydrogen peroxide producing vaginal *Lactobacillus* include most *L. crispatus* and *L. jensenii* strains, and approximately half of *L. gasseri* strains, as described in Antonio et al. *The Journal of Infectious Diseases* 1999, 180:1950-6.

$H_2O_2$ production by a *Lactobacillus* of the present invention can be quantitated by any means for measuring $H_2O_2$ production. Methods used to measure $H_2O_2$ production are well known in the art, and can include the culture method or the direct detection method. The culture method can involve measuring $H_2O_2$ production by quantifying the intensity of a blue pigment formed when *Lactobacillus* is inoculated onto tetramethylbenzidine medium (TMB) and incubated under anaerobic conditions. For example, *Lactobacillus* is incubated on a TMB agar plate for about 48 hours under anaerobic conditions at 37° C. The agar plate is then exposed to ambient air. Exposure to the ambient air causes the $H_2O_2$ produced by the *Lactobacillus* to react with horseradish peroxidase in the agar to oxidize the TMB, causing the

*Lactobacillus* colonies to turn blue. See, e.g., Antonio et al. *The Journal of Infectious Diseases* 1999; 180:1950-6. The direct detection method can be used to measure the quantity of $H_2O_2$ on a detection scale between 0 and 100 mg/L using commercially available $H_2O_2$ detection test trips (e.g., available from EM Sciences or Merck). See, e.g., Strus, M. et al. The in vitro activity of vaginal *Lactobacillus* with probiotic properties against Candida. *Infect Dis Obstet Gynecol.* 2005 June; 13(2):69-75.

Another identifying characteristic of a *Lactobacillus* suitable for use in a medicant of the present invention is the genetic identity and stability of the *Lactobacillus* strain over time both in vivo and in vitro. According to the present invention, genetic stability refers to the ability of successive generations of a *Lactobacillus* strain to substantially maintain the identical genetic profile of the mother strain. In other words, successive generations of a genetically stable strain will not acquire substantial mutations in its genomic DNA over a period of time. Repetitive Sequence Polymerase Chain Reaction (Rep PCR) can be used to confirm genetic identity and stability of a strain of *Lactobacillus* over time after either in vitro storage or in vivo colonization of vaginal epithelial cells. Rep PCR methods used to confirm genetic identity and stability *Lactobacillus* strains are well known in the art and can be found in U.S. Pat. No. 6,093,394. See also, Antonio & Hillier, *J. Clin. Microbiol.* 2003, 41:1881-1887.

Another identifying characteristic of a *Lactobacillus* suitable for use in a medicant of the present invention is the ability to produce lactic acid. Lactic acid has been shown to inhibit the growth of pathogens in vitro. Preferably, a *Lactobacillus* produces at least about 0.75 mg/100 mL lactic acid, and more preferably at least about 4 mg/100 mL lactic acid, and even more preferably at least about 8.8 mg/100 mL lactic acid under effective growth conditions.

A suitable *Lactobacillus* strain can have a relatively large cell size. As provided in Bergey's Manual of Determinative Bacteriology, typical *Lactobacillus* are 0.8-1.6 μm in width and 2.3-11 μm in length. A preferred *Lactobacillus* strain for use in the present invention has a cell size of from about 1 to about 2 microns in width and from about 2 to about 4 microns in length. Without being bound by theory, the present inventors believe that the large dimensions exhibited by cells of a *Lactobacillus* strain of the present invention may allow it to better serve as a protective agent in biocompetitive exclusion. Biocompetitive exclusion refers to the ability of the medical powder strain or strains of the present invention to competitively inhibit the growth of undesired bacterial strains. Such exclusion is attributed to the occupation of available space on a vaginal epithelial cell by the beneficial *Lactobacillus* cells (e.g., the medical powder strain), thus preventing attachment of pathogenic, or undesirable, microbial cells.

In addition to known species and strains of *Lactobacillus*, newly identified species and strains from nature and mutant strains derived from known or newly identified strains can be used in a medicant of the present invention. Mutants of a parental strain of *Lactobacillus* that have the identifying characteristics of a *Lactobacillus* suitable for use in a medicant of the present invention can be obtained by, for example, subjecting a parental strain to at least one round of chemical and/or radiation mutagenesis, to increase the rate of mutagenesis, thereby increasing the probability of obtaining a microorganism having improved desired characteristics. It will be obvious to one of skill in the art that mutant microorganisms of the present invention also include microorganisms that can be obtained by genetically engineering microorganisins to, for example, have increased percent VEC cohesion values. As used herein, a "mutated microorganism" is a mutated parental microorganism in which the nucleotide composition of such microorganism has been modified by mutation(s) that occur naturally, that are the result of exposure to a mutagen, or that are the result of genetic engineering.

Preferred species of *Lactobacillus* include *Lactobacillus crispatus, Lactobacillus gasseri* and *Lactobacillus jensenii*, or a species of *Lactobacillus* having 95% sequence homology to the 16S rRNA gene sequence of any of the identified species. Particularly preferred strains of lactobacilli are strains having all the identifying characteristics of the *Lactobacillus crispatus* CTV-05 strain, *Lactobacillus crispatus* SJ-3C strain. *Lactobacillus crispatus* CTV-05 is a preferred strain. Methods used to differentiate between *Lactobacillus* strains include Rep-PCR, as described in Antonio & Hillier, *J. Clin. Microbiol.* 2003, 41:1881-1887, multilocus sequence typing (MLST), originally developed to identify strains of pathogens (see, e.g., Maiden, M. C., et. al 1998, Multilocus sequence typing: a portable approach to the identification of clones within populations of pathogenic microorganisms. *Proc. Natl. Acad. Sci. USA.,* 95:3140-2145), and whole genome sequencing.

Culturing Vaginal Bacteria

The *Lactobacillus* strains useful for the present invention can be grown in liquid or on solid media (e.g., agar). Bacterial media for growing *Lactobacillus* strains useful for the present invention are known and commercially available (e.g., from BD Difco) and include, e.g., de Man, Rogosa, and Sharpe (MRS) and Rogosa media. The *Lactobacillus* are preferably cultured anaerobically or microaerophilically and the temperature of the culture medium can be any temperature suitable for growth of *Lactobacillus. Lactobacillus* strains for the instant invention can be cultured in anaerobic conditions and are generally grown at about 37° C. Effective culture conditions for vaginal *Lactobacillus* strains useful for the instant invention are well known in the art. Specific culture conditions, culture media and methods of culturing *Lactobacillus* strains, particularly *L. crispatus* and *L. gasseri*, can be found in, e.g., U.S. Pat. No. 8,329,417, 6,093, 394, and Davis, C. Enumeration of probiotic strains: Review of culture-dependent and alternative techniques to quantify viable bacteria. *J Microbiol Methods.* 2014; 103:9-17.

The culture medium is inoculated with an actively growing culture of the *Lactobacillus* strain in an amount sufficient to produce, after a reasonable growth period, a suitable cell density (or potency) for transfer to the preservation medium. A non-limiting example of a reasonable growth period of the *Lactobacillus* used herein is a generation time of between 1 to 2.5 hours. The cells are grown to a preferred cell density in the range of from about $10^8$ CFU/mL to about $10^{10}$ CFU/mL. A culture-based method is used to determine the cell density, in which serial dilutions of *Lactobacillus* cultures are plated onto MRS agar plates and incubated for 48 hr anaerobically at 37° C. Colonies on the plates are counted and the number of CFUs (colony forming units) in the samples are calculated as CFU/mL or CFU/gram. Methods of determining the CFUs are described in detail below.

Once the cells are grown to preferred cell density, the bacterial cells can be harvested using any suitable method to remove the cells from the culture media. Non-limiting exemplary methods for harvesting the cultured cells includes, filtration, centrifugation, and sedimentation. In some examples, harvesting cultured cells can involve hollow fiber filtration and washing via diafiltration. Methods for harvesting cultured *Lactobacillus* cells are well known in the art and are described in detail in the Examples section. After separation of the cells from the culture media and/or washing of the biomass, the cells to centrifuged to form a cell pellet in preparation for suspension in a preservation medium.

Preparation of the Aqueous Preservation Medium

The bacterial cell pellet formed from the methods described above is resuspended in a suitable aqueous preservation medium, where the weight ratio of cell pellet wet weight (grams) to preservation media (mL) can be between 1:1 and 1:8 grams of cell pellet to milliliter of preservation media. In some embodiments, the bacterial cell pellet is resuspended in a suitable aqueous preservation medium, where the weight ratio of cell pellet wet weight (grams) to preservation media (mL) can be between 1:1 and 1:7 grams of cell pellet to milliliter of preservation media, or between 1:1 and 1:6, or between 1:1 and 1:5, or between 1:1 and 1:4, or between 1:1 and 1:3, or between 1:1 and 1:2, or between 1:2 and 1:6, or between 1:3 and 1:5 grams of cell pellet to milliliter of preservation media. In some embodiments, the bacterial cell pellet is resuspended in a suitable aqueous preservation medium, where the weight ratio of cell pellet wet weight (grains) to preservation media (mL) can be 1:1, 1:2, 1:3, 1:4, 1:5, 1:6, 1:7, or 1:8 grams of cell pellet to milliliter of preservation media. In some embodiments, the bacterial cell pellet is resuspended in a suitable aqueous preservation medium, where the weight ratio of cell pellet wet weight (grams) to preservation media (mL) can be between 1:1 and 1:5 grams of cell pellet to milliliter of preservation media. In some embodiments, the bacterial cell pellet is resuspended in a suitable aqueous preservation medium, where the weight ratio of cell pellet wet weight (grams) to preservation media (mL) can be between 1:1 and 1:3 grams of cell pellet to milliliter of preservation media.

The aqueous preservation medium is comprised of ingredients that minimize the damaging effects encountered during the preservation process. The preservation medium of this invention includes a carbohydrate, a polyol, an antioxidant, a buffering agent, and, optionally, an amino acid. The carbohydrate used in the preservation medium functions as a lyoprotectant to protect and stabilize the cells during freeze drying, and afterwards during storage. Non-limiting exemplary carbohydrates suitable for use with the invention include trehalose, dextrose, lactose, maltose, sucrose and/or any other disaccharide or polysaccharide. In some embodiments, the preservation medium comprises from about 0.5% to about 30% carbohydrate by weight per volume (w/v) of the preservation medium, or from about 1% to about 25%, or from about 5% to about 20%, or from about 10% to about 15% carbohydrate by w/v of the preservation medium. In some embodiments, the preservation medium comprises from about 0.5% carbohydrate by weight per volume (w/v) of the preservation medium, or from about 1, 2, 5, 7, 10, 15, 20, 25, or 30% carbohydrate by w/v of the preservation medium. In some embodiments, the preservation medium comprises from about 5% to about 20% trehalose w/v of the preservation medium. In some other embodiments of the invention, the preservation medium comprises from about 5% to about 15% trehalose w/v of the preservation medium.

The polyol (i.e., polyhydric alcohol) of the preservation medium is a lyoprotectant that helps protect cells from the stresses of dehydration during freeze drying. Non-limiting exemplary polyols suitable for use with the present invention include xylitol, adonitol, glycerol, dulcitol, inositol, mannitol, maltitol, isomalt, lactitol, erythritol, sorbitol and/or arabitol. In some embodiments, the preservation medium comprises from about 0.1% to about 12% polyol by weight per volume (w/v) of the preservation medium, or from about 1% to about 10%, or from about 2% to about 9%, or from about 3% to about 7% polyol by w/v of the preservation medium. In some embodiments, the preservation medium comprises from about 0.1% polyol by weight per volume (w/v) of the preservation medium, or from about 0.5, 1, 2, 3, 5, 6, 7, 8, 9, 10, 11, or 12% polyol by w/v of the preservation medium. In some embodiments, the preservation medium comprises from about 2% to about 9% xylitol w/v of the preservation medium. In some other embodiments of the invention, the preservation medium comprises from about 2% to about 7% xylitol w/v of the preservation medium.

The antioxidant of the preservation medium retards oxidative damage to the microbial cells during the preservation and storage process. Non-limiting exemplary antioxidants suitable for use with the instant invention include sodium ascorbate, ascorbic acid, palmityl ascorbate, propyl gallate and vitamin E (α-tocopherol). In some embodiments, the preservation medium comprises from about 0.1% to about 5% antioxidant by weight per volume (w/v) of the preservation medium, or from about 0.5% to about 3.0%, or from about 1.0% to about 2.0% antioxidant by w/v of the preservation medium. In some embodiments, the preservation medium comprises from about 0.1% antioxidant by weight per volume (w/v) of the preservation medium, or from about 0.3, 0.5, 1.0, 1.5, 2.0, 2.5, 3.0, 3.5, 4.0, 4.5, or 5.0% antioxidant by w/v of the preservation medium. In some embodiments, the preservation medium comprises from about 0.5% to about 1.5% sodium ascorbate w/v of the preservation medium. In some other embodiments of the invention, the preservation medium comprises from about 0.5% to about 1.5% sodium ascorbate w/v of the preservation medium.

Buffering agents suitable for use in the preservation medium enhance the stability and recovery of the bacteria cells. A buffering agent suitable for use in the preservation medium is a physiological agent that does not exert any toxic effects on the bacteria, vaginal epithelial cells or a female patient using a pharmaceutical composition. Non-limiting exemplary buffering agents suitable for use with the instant invention include sodium phosphate, disodium phosphate, potassium phosphate, sodium bicarbonate, histidine, arginine and sodium citrate. In some embodiments, the buffering agent can have a pKa of from about 4.3 to about 8.0, or from about 4.6 to about 7.7, or from about 5.0 to about 7.3, or from about 5.4 to about 7.0, or from about 6.0 to about 6.7. In some other embodiments, the preservation medium comprises a buffering solution having a pKa of at least 4.3, 4.4, 4.5, 4.6, 4.7, 4.8, 4.9, 5.0, 5.5, 6.0, 6.5, 7.0, 7.5, 8.0, or higher. In some embodiments, the preservation medium comprises a buffering solution having a pKa in the physiological range. In other embodiments, the preservation medium comprises a buffering solution having a pKa of from about 6.7 to about 7.8.

In still further embodiments, the preservation medium comprises from about 5 mM to about 70 mM buffering agent, or from about 10 mM to about 65 mM, or from about 15 mM to about 60 mM, or from about 20 mM to about 55 mM, or from about 25 mM to about 50 mM, or from about 30 mM to about 45 mM, or from about 35 mM to about 40 mM buffering agent. In some embodiments, the preservation medium comprises from about 5 mM buffering agent, or from about 10, 15, 20, 25, 30, 35, 40, 45, 50, 55, 60, 65 or 70 mM. In some embodiments, the preservation medium comprises from about 10 mM to about 50 mM sodium phosphate. In some other embodiments of the invention, the preservation medium comprises horn about 10 mM to about 30 mM sodium phosphate.

In some embodiments, the preservation medium can optionally include an amino acid that helps enhance stability of the *Lactobacillus* cells at elevated temperatures without significantly affecting cryopreservation during the lyophilization process. In some embodiments, the optional amino acid can be in the salt form of a suitable amino acid. Non-limiting exemplary amino acids and/or their salts suitable for use with the instant invention include sodium glutamate, glutamine, glycine, arginine, histidine, and lysine. In some embodiments, the preservation medium optionally comprises from about 0% to about 5% amino acid by weight per volume (w/v) of the preservation medium, or from about 0.5% to about 3.0%, of from about 1.0% to about 2.0% amino acid by w/v of the preservation medium. In some embodiments, the preservation medium optionally comprises from about 0.1% amino acid by weight per volume (w/v) of the preservation medium, or from about 0.3, 0.5, 1.0, 1.5, 2.0, 2.5, 3.0, 3.5, 4.0, 4.5, or 5.0% amino acid by w/v of the preservation medium. In some embodiments, the amino acid optionally included in the preservation medium is amino acid salt sodium glutamate, preferably monosodium glutamate. In some embodiments, the preservation medium optionally comprises from about 0% to about 5% sodium glutamate w/v of the preservation medium. In some other embodiments of the invention, the preservation medium optionally comprises from about 0% to about 5% monosodium glutamate w/v of the preservation medium. In some embodiments, the preservation medium optionally comprises from about 1% to about 4% sodium glutamate w/v of the preservation medium. In some other embodiments of the invention, the preservation medium optionally comprises from about 1% to about 4% monosodium glutamate w/v of the preservation medium.

The preservation medium of the present invention includes a carbohydrate that is between about 5% and 20% of the preservation medium by weight per volume, a polyol that is between about 2% and 9% of the preservation medium by weight per volume, an antioxidant that is between about 0.5% and 1.5% of the preservation medium by weight per volume and a buffering agent that is between 10 mM and 50 mM. In other embodiments, a preservation medium suitable for use with the present invention can include a carbohydrate that is between about 5% and 15% of the preservation medium by weight per volume, a polyol that is between about 2% and 7% of the preservation medium by weight per volume, an antioxidant that is between about 0.5% and 1.0% of the preservation medium by weight per volume and a buffering agent that is between 10 mM and 30 mM.

In some embodiments, the preservation medium of the present invention includes a carbohydrate that is between about 5% and 20% of the preservation medium by weight per volume, a polyol that is between about 2% and 9% of the preservation medium by weight per volume, an antioxidant that is between about 0.5% and 1.5% of the preservation medium by weight per volume, a buffering agent that is between 10 mM and 50 mM, and, optionally, an amino acid that is between about 0% and 5% of the preservation medium by weight per volume. In other embodiments, a preservation medium suitable for use with the present invention can include a carbohydrate that is between about 5% and 15% of the preservation medium by weight per volume, a polyol that is between about 2% and 7% of the preservation medium by weight per volume, an antioxidant that is between about 0.5% and 1.0% of the preservation medium by weight per volume, a buffering agent that is between 10 mM and 30 mM and, optionally, an amino acid that is between about 0% and 5% of the preservation medium by weight per volume.

An example of a particularly useful preservation medium of the present invention includes trehalose as the carbohydrate that is between about 5% and 20% of the preservation medium by weight per volume, xylitol as the polyol that is between about 2% and 9% of the preservation medium by weight per volume, sodium ascorbate as the antioxidant that is between about 0.5% and 1.5% of the preservation medium by weight per volume and sodium phosphate as the buffering agent that is between 10 mM and 50 mM. In some embodiments, a particularly useful preservation medium of the present invention includes trehalose as the carbohydrate that is between about 5% and 20% of the preservation medium by weight per volume, xylitol as the polyol that is between about 2% and 9% of the preservation medium by weight per volume, sodium ascorbate as the antioxidant that is between about 0.5% and 1.5% of the preservation medium by weight per volume, sodium phosphate as the buffering agent that is between 10 mM and 50 mM and, optionally, sodium glutamate as the amino acid that is between about 0% and 5% of the preservation medium by weight per volume. In other embodiments, a preservation medium suitable for use with the present invention includes trehalose that is between about 5% and 15% of the preservation medium by weight per volume, xylitol that is between about 2% and 7% of the preservation medium by weight per volume, sodium ascorbate that is between about 0.5% and 1.0% of the preservation medium by weight per volume and sodium phosphate that is between 10 mM and 30 mM. In some other embodiments, a preservation medium suitable for use with the present invention includes trehalose that is between about 5% and 15% of the preservation medium by weight per volume, xylitol that is between about 2% and 7% of the preservation medium by weight per volume, sodium ascorbate that is between about 0.5% and 1.0% of the preservation medium by weight per volume, sodium phosphate that is between 10 mM and 30 mM, and, optionally, sodium glutamate that is between about 0% and 5% of the preservation medium by weight per volume. Representative preservation media compositions, which are in no way meant to be limiting, are included in Table 1 below.

TABLE 1

Exemplary preservation media compositions and ingredient ratios

| | Ingredient (%, w/w) | | | | |
|---|---|---|---|---|---|
| No. | Trehalose | Xylitol | Sodium ascorbate | $NaPO_4$ * | Sodium glutamate |
| i | 5-15 | 2-9 | 0.5-1.5 | 10-30 | 0-5 |
| ii | 5, 10, or 15 | 2 | 0.5 | 10 | 0-5 |
| iii | 7.5 | 2, 3, or 9 | 0.75 | 15 | 0-5 |
| iv | 7.5 | 3 | 0.5, 1.0, or 1.5 | 15 | 0-5 |
| v | 7.5 | 3 | 0.75 | 10, 12, or 15 | 0-5 |

* Amount of sodium phosphate is measured in mM

Prior to addition of the above described harvested *Lactobacillus* cells to the medium, the cells may be washed in a saline buffer. Upon introduction of the harvested *Lactobacillus* cells to the preservation medium described herein, the resulting mixture is referred to as the cell-preservation medium slurry. In some embodiments, a cell-preservation medium slurry can have an activity of between $10^8$ CFU/mL and $10^{11}$ CFU/mL. A more preferred cell-preservation medium slurry can have an activity of at least about $10^{10}$ CFU/mL. It is to be understood that one of ordinary skill in the art will appreciate variations to the basic culturing, harvesting and suspending steps disclosed herein and as such, the present invention incorporates such variations.

Drying the Cell-Preservation Medium Slurry

The cell-preservation medium slurry can be dried to produce the resulting bulk drug powder using any suitable drying method known in the art. Typically the effect of drying is to place the bacteria in a state of dormancy to protect the bacteria from environmental elements that negatively impact the viability of the bacteria. The standard way to bring about dormancy is through the removal of water. Generally, sufficient water is removed so that the normal cellular processes (e.g. enzymatic activity) come to a halt or are at least greatly diminished.

The cell-preservation medium slurry can be dried using any of the numerous methods known in the art for drying a bacterial preparation to increase their stability for long term storage. Drying methodologies and protective agents are disclosed in the review by Morgan et al. (2006) *J. Microbiol. Meth.* 66:183-193. Suitable drying methods include air drying, vacuum drying, oven drying, spray drying, flash drying, fluid bed drying, controlled atmosphere drying, and lyophilization (i.e., freeze drying). In some embodiments, a desiccant is used to aid in the drying process, and/or to prevent reabsorption of moisture into the dried formulation. In some embodiments, the drying is carried out using a lyophilizer (i.e., Virtis, SP Scientific). Detailed freeze-drying methods known to persons of skill in the art and are disclosed in U.S. Pat. Nos. 6,093,394; 8,329,447; and 8,642,029. The resulting dry formulation referred to as the bulk powder is tested for potency using the methods described below. The potency of the dry bulk drug powder can be between $10^9$ CFU/g and $10^{12}$ CFU/g. A more preferred bulk powder can have an activity of at least about $10^{10}$ CFU/g.

Measuring Residual Water

A dried formulation can be tested for the presence of residual water using any suitable method known in the art. In some cases, residual water in the dried formulation can be measured gravimetrically, as described in U.S. Pat. Nos. 8,329,447 and 8,642,029. Alternatively, an instrument for measuring water content in powders could be used to monitor the moisture content of the formulation during drying, e.g., the IR-120 Moisture Analyzer (Denver Instruments, Denver, Colo.). Residual water moisture can also be determined by performing well known coulometric or volumetric titration techniques, such as the Karl Fischer titration.

Water content in a *Lactobacillus* powder can also be measured as the free water or water activity ($a_w$) using a water activity meter, e.g., AquaLab CX-2 Model series (Decagon Instruments, Pullman, Wash.), or a Rotronic Model series (Rotronic Instillment Corp., Huntington, N.Y.). The water activity meter (AquaLab CX-2, Decagon Instruments) uses a chilled-mirror dew point technique to measure the $a_w$ of a product. When a sample is placed in the AquaLab, a stainless-steel mirror within the chamber is repeatedly cooled and heated while dew forms and is driven off. The instrument's fan circulates the air in the sensing chamber, speeding up the equilibration process. Each time dew forms on the mirror, AquaLab measures the temperature and calculates the $a_w$ of the sample, saving these values to compare to previous values. When the $a_w$ values of consecutive readings are less than 0.001 apart, the measurement process is complete.

The water energy level or water activity ($a_w$) determines the overall stability of the resulting dry bulk *Lactobacillus* drug powder. One of ordinary skill in the art will appreciate the importance of the water activity of pharmaceuticals, such as the $a_w$ of the drug powder of the invention. By maintaining a low water activity of a pharmaceutical product, degradation of the active pharmaceutical ingredient (i.e., the *Lactobacillus* drug powder) can be avoided. Furthermore, a pharmaceutical product, such as the *Lactobacillus* drug powder of the present invention, having a low water activity can be less susceptible to crystallization, caking and clumping, which contributes to the drug's degradation and ineffectiveness. These are time-dependent reactions with rates influenced by water activity. Details on the influence of $a_w$ on a product formulation can be found in United States Pharmacopeial Method <1112> Microbiological Attributes of Non-sterile Pharmaceutical Products—Application of Water Activity Determination.

In some embodiments, the dry bulk *Lactobacillus* drug substance can have a measured $a_w$ of from about 0.001 to about 0.220, or from about 0.005 to about 0.200, or from about 0.010 to about 0.150, or from about 0.025 to about 0.100, or from about 0.050 to about 0.075. In other embodiments, the dry bulk *Lactobacillus* drug substance can have a measured $a_w$ of from about 0.001, 0.003, 0.005, 0.007, 0.010, 0.030, 0.050, 0.070, 0.100, 0.150, 0.170, 0.200, 0.220. In particular embodiments, the dry bulk *Lactobacillus* drug substance can have a measured $a_w$ of less than 0.220.

Measuring Potency

The *Lactobacillus* formulations (wet and/or dry) of the present invention are tested for potency at different times throughout the preparation process using any suitable method known in the art. Such methods used to determine the potency that of the *Lactobacillus* formulations include, but are not limited to, the culture-based method. The light scattering method for determining cell density of *Lactobacillus* is used to monitor the fermentation process and involves measuring the optical density at 600 nm of a sample of bacteria.

The preferred method used to measure the potency of the *Lactobacillus* formulations is the culture-based method involving serial dilutions. A sample of the *Lactobacillus* formulation to be tested is obtained and serial dilutions are made. A small aliquot (i.e., 100 μL) of serial dilutions are plated onto MRS agar plates. The samples are allowed to incubate anaerobically at 37° C. for 48 hours. After a suitable amount of time has passed, the plates are illuminated by placing the Petri dishes in transmitted light. The separate colonies are counted manually or with a camera and computer using commercially available bacterial counting software, and the number of CFUs in the samples are calculated as CFU/ml or CFU/gram. More details involving the culture-based methods are disclosed in Brugger, S. D., et al. Automated Counting of Bacterial Colony Forming Units on Agar Plates. *PLOS ONE* 2012; 7(3): e33695.

Purity and Identity

In addition to measuring the potency and the water activity, the bulk drug powder produced from the above described drying methods can be tested for purity and identity. The purity of the bulk drug powder is determined using methods well known in the art and as described in United States Pharmacopeial Method <61> Microbial Enumeration Tests and United States Pharmacopeial Method <62> Tests for Specified Microorganisms. Genetic identification of the *Lactobacillus* species in the bulk powder and final drug product is carried out by isolating genomic DNA using a commercially available kit (e.g. Power Soil DNA Isolation Kit, Mo Bio), amplifying the 16S rRNA gene using specific primers by PCR, sequencing the gene using a commercial DNA sequencing service (MCLAB), and comparing the sequence to a reference standard. Identification of the *Lactobacillus* strain in the bulk drug powder is determined using methods well known in the art, such as Repetitive Sequence Polymerase Chain Reaction (Rep PCR) and as described in U.S. Pat. Nos. 6,093,3941; 8,329,447; and 8,642,029.

Diluting Bacterial Powder with Inactive Excipients

In order to adhere to the potency and dosage guidelines agreed upon and developed by the U.S. Food and Drug Administration (FDA), the activity of the bulk *Lactobacillus* drug powder is diluted using a pharmaceutically acceptable excipient. Any suitable inactive pharmaceutically acceptable excipient (i.e., diluent) known in the art can be used to dilute the potency of the *Lactobacillus* drug powder. In some embodiments, a diluent can be maltodextrin, pre-gelatinized starch, lactose, Pharmasperse®, mannitol, xylitol, microcrystalline cellulose, sugar or a combination thereof. In other embodiments, an inactive bulking agent can be used in combination with another diluent. In other embodiments, a maltodextrin or pre-gelatinized starch can be used to dilute the bulk lactobacilli drug powder. In some embodiments, maltodextrin is used to dilute the bulk lactobacilli drug powder.

In some embodiments, the bulk *Lactobacillus* drug powder is diluted with an inactive excipient by between 3-fold and 10-fold. In other embodiments, the bulk *Lactobacillus* drug powder can be combined with an inactive excipient at a ratio of powder to inactive excipient of between 1:1 and 1:12 w/w. In some embodiments, the bulk *Lactobacillus* drug powder can be combined with an inactive excipient at a ratio of powder to an inactive excipient of 1:1, 1:2, 1:3, 1:4, 1:5, 1:6, 1:7, 1:8, 1:9, 1:10, 1:11, or 1:12 w/v. In particular embodiments, the bulk *Lactobacillus* drug powder can be combined with an inactive excipient at a ratio of powder to an inactive excipient of between 1:1 and 1:10 w/w. In particular embodiments, the bulk *Lactobacillus* drug powder can be combined with an inactive excipient at a ratio of powder to an inactive excipient of between 1:1 and 1:5 w/w. In some embodiments, the bulk *Lactobacillus* drug powder can be combined with an inactive excipient at a ratio of powder to an inactive excipient of between 1:1 and 1:3 w/w.

In particular embodiments, the bulk *Lactobacillus* drug powder can be combined with maltodextrin at a ratio of powder to maltodextrin of between 1:1 and 1:10 w/w. In particular embodiments, the bulk *Lactobacillus* drug powder can be combined with maltodextrin at a ratio of powder to maltodextrin of between 1:1 and 1:5 w/w. In some embodiments, the bulk *Lactobacillus* drug powder can be combined with maltodextrin at a ratio of powder to maltodextrin of between 1:1 and 1:3 w/w. The potency of the diluted dry bulk *Lactobacillus* drug powder, referred to as the drug product, can be between $10^8$ CFU/g and $10^{11}$ CFU/g, or between $10^8$ CFU/g and $10^{10}$ CFU/g. A more preferred drug product can have an activity of greater than $10^9$ CFU/g.

The drug product can be packaged in dosages of between about 100 mg and 600 mg. In some embodiments, the drug product dosage can be packaged in a dosage of about 100 mg, or of about 150, 200, 250, 300, 350, 400, 450, 500, 550, or 600 mg. In other embodiments, the drug product can be packaged in dosages of between about 150 mg and 450 mg, or about 150 mg and about 400 mg, or about 150 mg and about 350 mg. In some embodiments, the drug product can be packaged in dosages of between about 150 mg and 250 mg. In a particular embodiment, the drug product can be packaged in a dosage of about 200 mg.

The drug product can be placed in a medical powder applicator, referred to as the final drug product, and packaged to protect against moisture and oxygen during transport and storage. The package can be comprised of any suitable material for such protection such as Mylar or metallic film pouches. In some embodiments, the final drug product is sealed into individual packages, e.g., for individual dosages.

Using the Dry Preserved *Lactobacillus* Final Drug Product

The final drug product (i.e., dry powder) of any suitable *Lactobacillus* species and strain, as described herein, can be used to prevent and/or treat a vaginal infection (i.e., abnormal vaginal microbiota). Such vaginal infections include, but are not limited to, bacterial vaginosis, yeast vaginitis, gonorrhea, *chlamydia*, trichomoniasis, human immunodeficiency virus infection, herpes simplex virus type 2 (HSV-2), urinary tract infection, and pelvic inflammatory disease. In some embodiments, the final drug product can be used to prevent and/or treat bacterial vaginosis, yeast vaginitis, or urinary tract infection. In a particular embodiment, the dry powder can be used to prevent and/or treat bacterial vaginosis (BV).

Abnormal vaginal microbiota can be detected and diagnosed using any suitable means known in the art. A vaginal infection can be symptomatic or asymptomatic. Symptoms generally include abnormal odor and/or discharge, and discomfort from itching and/or pain. Depending on the vaginal infection, it can be detected by a woman without medical consultation or diagnostic apparatuses or kits. For example, a few inexpensive, non-prescription kits for detecting yeast vaginitis are available (e.g., Vagisil™).

In some cases, medical practitioners will detect and diagnose the vaginal infection. Clinical criteria require the presence of at least three symptoms, including those mentioned above, a vaginal fluid pH of >4.5, and the presence of clue cells (e.g., vaginal epithelial cells studded with adherent coccobacilli) on microscopic examination. For example, bacterial vaginosis can be detected, e.g., by Amsel clinical criteria or Gram stained vaginal smears (Nugent scoring system). The Gram stained vaginal smear is used to determine the relative concentration of lactobacilli (Gram-positive bacteria), Gram-negative and Gram-variable rods and cocci (i.e., *G. vaginalis, Prevotella, Porphyromonas*, and peptostreptococci), and curved Gram-negative rods (i.e., *Mobiluncus*) characteristic of BV. Detection and diagnostic methods for various vaginal infections are well known in the art and are described in U.S. Pat. No. 8,329,147. See also https://www.cdc.gov/std/tg2015/bv.htm.

The dry powder of the present invention can be administered alone or in combination with (e.g., simultaneously with, before, and or after) any other therapy for the prevention and/or treatment of vaginal infections. Administration of any other therapy for the prevention and/or treatment of vaginal infections can be administered in an amount effective to reduce the level of abnormal vaginal microbiota. Other therapies for the prevention and/or treatment of vaginal infections can include antibiotics or antiviral agents, which are well known in the art. In some embodiments, the other therapy for the prevention and/or treatment of vaginal infections can be an antibiotic. Suitable antibiotics for the prevention and/or treatment of abnormal vaginal microbiota are well known in the art. Such antibiotics include, but are not limited to, clindamycin, metronidazole, and tinidazole. An antibiotic for use in conjunction with the dry powder of the invention can be in any suitable form for administration. For example, an antibiotic can be delivered topically (as a gel or cream), or as an oral or vaginal tablet, capsule or suppository. In a particular embodiment, the antibiotic is administered as a topical gel.

The antibiotic treatment can be administered between 1 and 2 times per day. In a particular embodiment, the antibiotic treatment can be administered 1 time per day.

In some embodiments of the invention, the antibiotic can be administered for between 2 and 7 days. In other embodiments, the antibiotic can be administered for 2, 3, 4, 5, 6, and 7 days. In some other embodiments, the antibiotic can be administered for between 2 and 7 days, or 3 and 6 days, or 4 and 5 days, or 4 and 7 days. In particular embodiments, the antibiotic can be administered for between 2 and 7 days. In another embodiment, the antibiotic can be administered for 7 days. In another embodiment, the antibiotic can be administered for 5 days.

In some embodiments, the administration of the dry powder is during the final few days of the administration regimen of an antibiotic (i.e., 2 to 4 days before the completion of the administration regimen of an antibiotic). In other embodiments, the dry powder is administered after the completion of the administration regimen of an antibiotic. The dry powder can be administered 1 or 2 times per day after the completion of the administration regimen of an antibiotic. In some embodiments, the dry powder can be administered 2 times per day after the completion of the administration regimen of an antibiotic. In a particular embodiment, the dry powder can be administered 1 time per day after the completion of the administration regimen of an antibiotic.

In some embodiments of the invention, the dry powder can be administered for between 1 and 14 days after the completion of the administration regimen of an antibiotic. In other embodiments, the dry powder can be administered for 1, 2, 3, 4, 5, 6, 7, 10, 12, or 14 days after the completion of the administration regimen of an antibiotic. In some other embodiments, the dry powder can be administered for between 2 and 12 days, or 3 and 10 days, or 4 and 7 days, or 5 and 6 days after the completion of the administration regimen of an antibiotic. In particular embodiments, the dry powder can be administered for between 5 and 7 days after the completion of the administration regimen of an antibiotic. In another embodiment, the dry powder can be administered for 5 days after the completion of the administration regimen of an antibiotic.

After completion of the antibiotic administration regimen and the initial dry powder administration regimen, the dry powder of the present invention can be administered for an additional period of time. For example, following the completion of the initial treatment using the dry powder (i.e., 1 dose per day for 7 days), the thy powder can be administered between 1 and 5 times per week. In some embodiments, the dry powder can be administered 1, 2, 3, 4, or 5 times per week after the completion of the initial dry powder treatment regimen. In other embodiments, the dry powder can be administered between 1 and 4 times per week, or between 2 and 5 times per week, or between 1 and 3 times per week, or between 1 and 2 times per week after the completion of the initial dry powder treatment regimen. In a particular embodiment, the dry powder can be administered 1 time per week after the completion of the initial dry powder treatment regimen.

In some embodiments of the invention, the dry powder can be administered for between 1 and 26 weeks after the completion of the initial dry powder treatment regimen. In other embodiments, are dry powder can be administered for 1, 2, 3, 4, 5, 6, 7, 8, 10, 12, 14, 16, 18, 20, 22, 24, or 26 weeks after the completion of the initial dry powder treatment regimen. In some other embodiments, the dry powder can be administered for between 2 and 26 weeks, or 3 and 24 weeks, or 4 and 22 weeks, or 5 and 20 weeks, or 6 and 18 weeks, or 7 and 16 weeks, or 8 and 14 weeks, or 10 and 12 weeks after the completion of the initial dry powder treatment regimen. In particular embodiments, the dry powder can be administered for between 5 and 10 weeks after the completion of the initial dry powder treatment regimen. In another embodiment, the dry powder can be administered for 10 weeks after the completion of the initial dry powder treatment regimen.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

IV. Examples

The following examples are provided by way of illustration only and not by way of limitation. Those of skill will readily recognize a variety of noncritical parameters which could be changed or modified to yield essentially similar results.

Example 1. Preparing the Dry Composition of *Lactobacillus*

This example details the general strategy for preparing the dry composition of *Lactobacillus* in powder form as a medical product, involving bacterial cultivation, suspension in preservation medium, drying, dilution, and packaging. The procedure described here, for the culture and processing of *Lactobacillus crispatus* SJ-3C, is applicable for any microorganism suitable for use with the present invention.

The initial *Lactobacillus crispatus* SJ-3C (SJ-3C) cells can be obtained from the deposit American Type Culture Collection (ATCC) under ATCC number PTA-10138. A Master Cell Bank and Working Cell Bank of these cells are prepared and can be subsequently used in the preparation of the dry *Lactobacillus* compositions.

The SJ-3C cells are initially plated onto modified de Man, Rogosa and Sharpe (MRS) agar plates and grown under anaerobic conditions for 72 hours at 37° C. Cells from the plates are inoculated into 10 mL of modified MRS and incubated anaerobically for 24 hours at 37° C. This culture is then transferred to 490 mL of growth medium and incubated for 24 hours at 37° C., followed by transfer to 4.5 L of medium in a 5 L Bellco Bioreactor. The 5-liter culture is incubated anaerobically at 37° C. for an additional 24 hours to serve as the fermentor inoculum.

Fermentation is performed in a fermentor (100 L fermentor) at pH 6.0 in the presence of modified MRS medium sparged with nitrogen gas. Fermentation is initiated by addition of the inoculum and completed after approximately 15 hours when the cells reach early stationary phase and growth stops. At this point, glucose is depleted, lactic acid production stops, the optical density of the culture at 600 nm (OD600) remains constant and the cells are harvested.

Cells are harvested, concentrated, and washed by buffer exchange into phosphate-buffered saline (diafiltration) in a sterile closed hollow fiber system using a tangential flow membrane. When the residual lactate concentration reaches 10% of the starting value at harvest and pH of the permeate remains constant, the cells are aseptically removed from the harvest system and collected by centrifugation at 1500×g for 20 minutes, 2-8° C.).

Cell pellets are resuspended in a preservation medium solution, using 2.5 mL of preservation solution per gram of cell paste. The preservation medium solution contains 15% trehalose, 6% xylitol, and 1% sodium ascorbate in a 10 mM sodium phosphate buffer (pH 7.4), which is used to prepare batches of the harvested SJ-3C slurry. The resulting batches of the preservation medium cell slurry are to have calculated activities of between $1\times10^{10}$ CFU/mL and $5\times10^{10}$ CFU/mL. The slurry is transferred to sterile Lyoguard™ trays and lyophilized in a Virtis Genesis Lyophilizer. Viability of the cell slurry is determined prior to lyophilization by plate counting. The Lyoguard™ trays containing the cell cakes are placed in heat-sealed bags with desiccant and purged with nitrogen gas, and held at 2-8° C. until milling.

The SJ-3C bulk drug substance is produced by milling the lyophilized cell cakes with 0.5% colloidal silicon dioxide as an anti-caking agent using a cone mill. The bulk powder is purged with nitrogen ($N_2$) gas and stored with desiccant in a heat-sealed bag at 2-8° C. until used for manufacture of the drug product. The SJ-3C bulk drug substance is tested for purity, potency (CFU), identity, and residual moisture using the methods as described previously and those known to one of skill in the art. The ideal activity of the resultant batches of the dry SJ-3C bulk drug substance should be between $5\times10^{10}$ CFU/g and $1.0\times10^{11}$ CFU/g. The ideal water activity of the dry SJ-3C bulk drug substance should be <0.220. When tested for purity, the resulting SJ-3C bulk drug substance will contain <200 CFU/g of total aerobic counts, <20 CFU/g of total yeasts and molds, and an absence of objectionable organisms. The identity of the resulting SJ-3C bulk drug substance is confirmed by the 16S rRNA gene sequence.

The bulk drug substance is diluted by 3 to 10-fold with maltodextrin to give a final dose of $2\times10^9$ CFU/dose to $5\times10^9$ CFU/dose. The dose is 200 mg. One dose of the diluted drug substance is placed in a medical powder applicator and packaged as the final drug product.

Example 2. Formulation Studies of Preservation Media with and without Animal-Derived Excipients The following example demonstrates the development and identification of a preservation medium formulation without skim milk that exhibits with good room temperature stability for a dry powder *Lactobacillus crispatus*. The example illustrates the increased stability of a dry *Lactobacillus* powder when animal-derived excipients are eliminated from the preservation medium. The following procedure describing the formulation and development of the preservation medium culture using *Lactobacillus crispatus* CTV-05 is applicable for any microorganism suitable for use with the present invention.

For the preservation formulation development studies, *Lactobacillus crispatus* CTV-05 was grown in a modified MRS medium at pH 6.0 on a 1 L scale in a stirred bioreactor BioFlo 110 Fermentor and Bioreactor (New Brunswick Scientific, Edison, N.J.). A batch fermentation process was used and cells were harvested at early stationary phase when glucose consumption and lactic acid production were completed. The fermentation process generally yielded $1.0\times10^9$-$1.5\times10^9$ CFU/mL with >90% cell viability. The cells were recovered by centrifugation, washed with phosphate buffered saline, and mixed with one or more preservation matrices. The mixture was then freeze-dried in a Virtis Advantage lyophilizer.

Initially, the cryopreservation and accelerated stability of CTV-05 was evaluated in 16 preservation matrices containing different concentrations of excipients for preserving *Lactobacillus* including skim milk, trehalose, xylitol, ascorbic acid, α-tocopherol, and phosphate buffer (Table 2).

TABLE 2

Composition of preservation matrices containing skim milk

| No. | Ingredient (%, w/w) Sodium ascorbate | α-Tocopherol | Xylitol | Skim milk | Trehalose | $NaPO_4$* |
|---|---|---|---|---|---|---|
| 1 | 0.1 | 0.2 | 2 | 5.0 | 5.0 | 10 |
| 2 | 1.0 | 0.2 | 2 | 15 | 5.0 | 10 |
| 3 | 0.1 | 1.2 | 2 | 15 | 15 | 10 |
| 4 | 1.0 | 1.2 | 2 | 5.0 | 15 | 10 |
| 5 | 0.1 | 0.2 | 6 | 15 | 15 | 10 |
| 6 | 1.0 | 0.2 | 6 | 5.0 | 15 | 10 |
| 7 | 0.1 | 1.2 | 6 | 5.0 | 5.0 | 10 |
| 8 | 1.0 | 1.2 | 6 | 15 | 5.0 | 10 |
| 9 | 0.1 | 0.2 | 2 | 5.0 | 15 | 20 |
| 10 | 1.0 | 0.2 | 2 | 15 | 15 | 20 |
| 11 | 0.1 | 1.2 | 2 | 15 | 5.0 | 20 |
| 12 | 1.0 | 1.2 | 2 | 5.0 | 5.0 | 20 |
| 13 | 0.1 | 0.2 | 6 | 15 | 5.0 | 20 |
| 14 | 1.0 | 0.2 | 6 | 5.0 | 5.0 | 20 |
| 15 | 0.1 | 1.2 | 6 | 5.0 | 15 | 20 |
| 16 | 1.0 | 1.2 | 6 | 15 | 15 | 20 |

*Amount of sodium phosphate is measured in mM

The samples were placed in serum vials and frozen at −40° C. for 5 hr, then subjected to primary drying at −40° C. under vacuum for 30 hr and secondary drying at 25° C. for 20 hr. The samples were packaged in foil pouches with desiccant and stored at 37° C. Powder samples were removed at regular intervals and viability (i.e., activity) measured by plating on MRS agar and colony counting at 0, 10, and 30 days. As shown in Table 3, formulations #6 and #16 exhibited the best storage stability at 37° C. (70%-75% retention of initial viability).

TABLE 3

Stability of CTV-05 in preservation matrices containing skim milk at 37° C.

| No. | CFU/g at $T_0$ | CFU/g at $T_{10}$ | CFU/g at $T_{30}$ | $T_{30}$ stability (% of $T_0$ activity) |
|---|---|---|---|---|
| 1 | $4.62\times10^{10}$ | $3.17\times10^{9}$ | $2.05\times10^{9}$ | 4.4 |
| 2 | $2.34\times10^{10}$ | $8.24\times10^{9}$ | $4.20\times10^{9}$ | 17.9 |

TABLE 3-continued

| Stability of CTV-05 in preservation matrices containing skim milk at 37° C. | | | | |
|---|---|---|---|---|
| No. | CFU/g at $T_0$ | CFU/g at $T_{10}$ | CFU/g at $T_{30}$ | $T_{30}$ stability (% of $T_0$ activity) |
| 3 | $1.04 \times 10^{10}$ | $1.11 \times 10^9$ | $5.49 \times 10^8$ | 5.3 |
| 4 | $1.69 \times 10^{10}$ | $3.78 \times 10^9$ | $2.15 \times 10^9$ | 12.7 |
| 5 | $8.99 \times 10^9$ | $6.80 \times 10^9$ | $4.05 \times 10^9$ | 45.1 |
| 6 | $1.60 \times 10^{10}$ | $1.51 \times 10^{10}$ | $1.13 \times 10^{10}$ | 70.6 |
| 7 | $2.43 \times 10^{10}$ | $2.43 \times 10^8$ | $7.41 \times 10^7$ | 0.3 |
| 8 | $2.10 \times 10^{10}$ | $9.41 \times 10^9$ | $6.27 \times 10^9$ | 29.9 |
| 9 | $2.18 \times 10^{10}$ | $2.06 \times 10^9$ | $3.62 \times 10^8$ | 1.7 |
| 10 | $1.21 \times 10^{10}$ | $6.56 \times 10^9$ | $3.05 \times 10^9$ | 25.2 |
| 11 | $1.54 \times 10^{10}$ | $1.82 \times 10^9$ | $6.04 \times 10^8$ | 3.9 |
| 12 | $2.07 \times 10^{10}$ | $4.52 \times 10^9$ | $1.86 \times 10^9$ | 9 |
| 13 | $2.14 \times 10^{10}$ | $1.14 \times 10^{10}$ | $5.32 \times 10^9$ | 24.9 |
| 14 | $3.80 \times 10^{10}$ | $1.59 \times 10^{10}$ | $4.68 \times 10^9$ | 12.3 |
| 15 | $9.79 \times 10^9$ | $5.65 \times 10^9$ | $3.70 \times 10^9$ | 37.8 |
| 16 | $7.34 \times 10^9$ | $7.32 \times 10^9$ | $5.55 \times 10^9$ | 75.6 |

A similar experiment was performed using the same 16 for described above, with the skim milk component removed (Table 4).

TABLE 4

| Composition of preservation matrices without skim milk | | | | | |
|---|---|---|---|---|---|
| | Ingredient (%, w/w) | | | | |
| No. | Sodium ascorbate | α-Tocopherol | Xylitol | Trehalose | $NaPO_4$ * |
| 1 | 0.1 | 0.2 | 2 | 5.0 | 10 |
| 2 | 1.0 | 0.2 | 2 | 5.0 | 10 |
| 3 | 0.1 | 1.2 | 2 | 15 | 10 |
| 4 | 1.0 | 1.2 | 2 | 15 | 10 |
| 5 | 0.1 | 0.2 | 6 | 15 | 10 |
| 6 | 1.0 | 0.2 | 6 | 15 | 10 |
| 7 | 0.1 | 1.2 | 6 | 5.0 | 10 |
| 8 | 1.0 | 1.2 | 6 | 5.0 | 10 |
| 9 | 0.1 | 0.2 | 2 | 15 | 20 |
| 10 | 1.0 | 0.2 | 2 | 15 | 20 |
| 11 | 0.1 | 1.2 | 2 | 5.0 | 20 |
| 12 | 1.0 | 1.2 | 2 | 5.0 | 20 |
| 13 | 0.1 | 0.2 | 6 | 5.0 | 20 |
| 14 | 1.0 | 0.2 | 6 | 5.0 | 20 |
| 15 | 0.1 | 1.2 | 6 | 15 | 20 |
| 16 | 1.0 | 1.2 | 6 | 15 | 20 |

* Amount of sodium phosphate is measured in mM

As shown below in Table 5, formulations #6 and #16 without skim milk exhibited similar initial potencies and the highest storage stability at 37° C. (~25%) of initial viability).

TABLE 5

| Stability of CTV-05 in preservation matrices without skim milk at 37° C. | | | | |
|---|---|---|---|---|
| No. | CFU/g at $T_0$ | CFU/g at $T_{10}$ | CFU/g at $T_{31}$ | $T_{31}$ stability (% of $T_0$ activity) |
| 1 | $6.70 \times 10^{10}$ | $1.50 \times 10^9$ | $2.03 \times 10^8$ | 0.3 |
| 2 | $8.10 \times 10^{10}$ | $1.09 \times 10^{10}$ | $2.90 \times 10^9$ | 3.6 |
| 3 | $3.00 \times 10^{10}$ | $1.89 \times 10^9$ | $8.61 \times 10^8$ | 2.9 |
| 4 | $3.77 \times 10^{10}$ | $9.09 \times 10^9$ | $2.80 \times 10^9$ | 7.4 |
| 5 | $3.16 \times 10^{10}$ | $4.41 \times 10^9$ | $7.79 \times 10^8$ | 2.5 |
| 6 | $3.07 \times 10^{10}$ | $1.32 \times 10^{10}$ | $7.36 \times 10^9$ | 24 |
| 7 | $7.53 \times 10^{10}$ | $1.36 \times 10^8$ | $7.90 \times 10^6$ | 0.01 |
| 8 | $6.45 \times 10^{10}$ | $1.66 \times 10^9$ | $5.47 \times 10^7$ | 0.08 |
| 9 | $2.77 \times 10^{10}$ | $1.91 \times 10^9$ | $2.82 \times 10^8$ | 1.0 |
| 10 | $3.00 \times 10^{10}$ | $5.52 \times 10^9$ | $1.68 \times 10^9$ | 5.6 |

TABLE 5-continued

| Stability of CTV-05 in preservation matrices without skim milk at 37° C. | | | | |
|---|---|---|---|---|
| No. | CFU/g at $T_0$ | CFU/g at $T_{10}$ | CFU/g at $T_{31}$ | $T_{31}$ stability (% of $T_0$ activity) |
| 11 | $4.87 \times 10^{10}$ | $6.91 \times 10^8$ | $1.92 \times 10^8$ | 0.39 |
| 12 | $4.80 \times 10^{10}$ | $5.42 \times 10^9$ | $5.19 \times 10^9$ | 10.8 |
| 13 | $6.07 \times 10^{10}$ | $2.69 \times 10^8$ | $4.09 \times 10^7$ | 0.067 |
| 14 | $5.69 \times 10^{10}$ | $2.02 \times 10^9$ | $2.30 \times 10^8$ | 0.4 |
| 15 | $2.49 \times 10^{10}$ | $2.84 \times 10^9$ | $6.56 \times 10^8$ | 2.6 |
| 16 | $2.60 \times 10^{10}$ | $1.39 \times 10^{10}$ | $6.66 \times 10^9$ | 25.6 |

While skim milk in Formulations #6 and #16 appeared to improve the storage stability, higher concentrations of sodium ascorbate and xylitol also appeared to improve the storage stability. However, higher concentrations of α-tocopherol did not seem to improve the storage stability of CTV-05, and subsequent experiments demonstrated that removal of α-tocopherol (and its vehicle, Tween 20) led to improved stability of CTV-05.

Following the removal of α-tocopherol (and Tween 20) from the preservation matrix of Formulation 6 in Table 2 above, it was determined that skim milk could also be removed without adversely affecting cryoprotection during freeze-drying or long term storage stability at 25° C. (FIG. 1). Thus, the best combination of cryoprotection and room temperature stability was achieved using a preservation solution containing 15% trehalose, 6% xylitol, 1% sodium ascorbate, and 10 mm sodium phosphate at pH 7.4 (FIG. 1, upper line). This formulation provided better stability than the same formulation containing 5% skim milk (FIG. 1, lower line).

Example 3. Use of Monosodium Glutamate to Improve Stability

Figure 2:
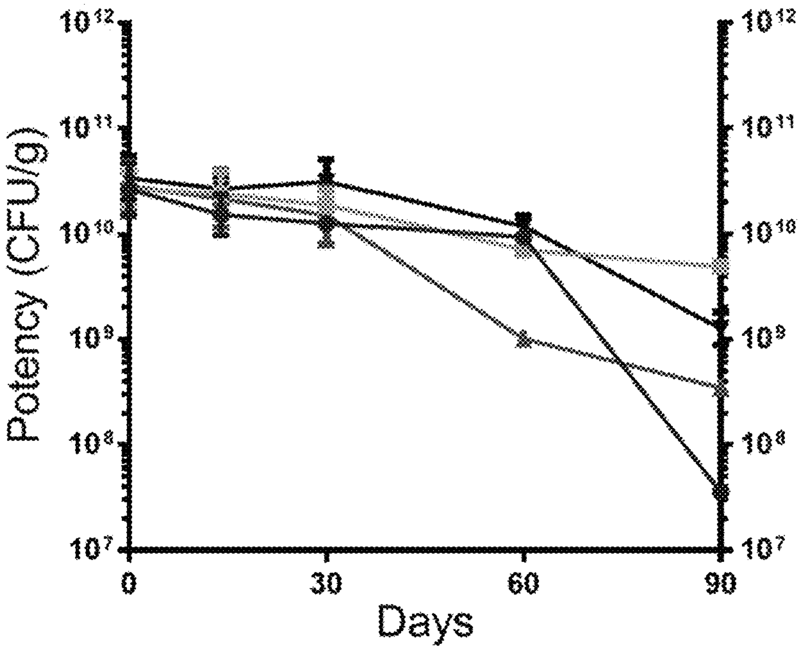
FIG. 2. *Lactobacillus* powder formulations with monosodium glutamate or without monosodium glutamate. The accelerated stability of four LACTIN-V formulations without monosodium glutamate (circles, triangles) or with monosodium glutamate (squares, inverted triangles) at 37° C. was determined by measuring viability over time. Powder samples were stored at 37° C. for 90 days and viability determined at different time points by culturing on MRS agar plates and counting colonies.

Following the procedure of Example 2, cultured *L. crispatus* CTV-05 (LACTIN-V) cells were formulated in four different preservation media: 1) 15% trehalose, 6% xylitol, 1% sodium ascorbate and 10 mM sodium phosphate at pH 7.4 (triangles); 2) the same preservation medium as 1), and additionally 5% monosodium glutamate (inverted triangles); 3) 12% trehalose, 8% xylitol, 1% sodium ascorbate and 10 mM sodium phosphate at pH 7.4 (circles); and 4) the same preservation medium as 3), and additionally 5% monosodium glutamate (squares). As shown in FIG. 2, the monosodium glutamate improved the stability of both powder formulations at elevated temperatures (37° C.), while having no effect on the initial cryopreservation.

Example 4. Use of a Dry Composition to Treat Abnormal Vagina/Microbiota

The example details an in vivo study which demonstrates that the *Lactobacillus* of the present invention can be used in vivo, delivered to the patient as a powder, to recolonize the vagina of women having recurrent bacterial vaginosis.

A 25-year old female patient having recurrent bacterial vaginosis (BV) is suffering from the symptoms of a BV infection, such as abnormal vaginal odor and discharge, and discomfort from itching and pain. BV is detected in the female patient by the Amsel clinical criteria (≥3 criteria satisfied), and confirmed microbiologically by the Nugent scoring system Nugent Score of 7-10).

The patient receives initial standardized antibiotic treatment with 0.75% topical metronidazole (MetroGel®) once a day for 5 days. After completion of the metronidazole treatment, the female patient begins treatment using the *Lactobacillus* SJ-3C drug product of the invention. A 200-mg dose of the SJ-3C drug product having an activity of $2\times10^9$ CFU per dose is administered to the patient vaginally using the packaged medical powder applicator. The patient receives a dose of the SJ-3C drug product once per day before sleeping for 5 consecutive days, followed by twice weekly treatments for 10 weeks.

What is claimed is:

1. An aqueous bacterial suspension of vaginal *Lactobacillus* species, having no animal-derived excipients, where the suspension results from a combination of a cell pellet of vaginal *Lactobacillus* species with an aqueous preservation medium consisting of:

(i) trehalose at between 5-20%, w/v;

(ii) xylitol at between 2-9%, w/v;

(iii) sodium ascorbate 0.5-1.5%, w/v; and (iv) sodium phosphate at between 10-50 mM.

2. The bacterial suspension of claim 1, wherein the vaginal *Lactobacillus* species has the ability to produce greater than 0.5 ppm of hydrogen peroxide under effective culture conditions.

3. The bacterial suspension of claim 1, wherein the vaginal *Lactobacillus* species is selected from the group consisting of *Lactobacillus crispatus, Lactobacillus jensenii* and *Lactobacillus gasseri.*

4. The bacterial suspension of claim 1, wherein the aqueous preservation medium consists of:

(i) trehalose at between 5-15%, w/v;

(ii) xylitol at between 2-7%, w/v;

(iii) sodium ascorbate 0.5-1.0%, w/v; and (iv) sodium phosphate at between 10-30 mM.

5. A dry powder obtained by lyophilizing the bacterial suspension of claim 1.

6. The dry powder of claim 5, wherein the powder has a water activity value of less than 0.220.

7. The dry powder of claim 6, wherein the powder is combined with an inactive excipient at a ratio of powder:excipient of between 1:1 and 1:10 w/w.

8. The dry powder of claim 7, wherein the excipient is maltodextrin.

9. The dry powder of claim 7, wherein the ratio of powder:excipient is between 1:1 and 1:5 w/w.

10. The dry powder of claim 5, wherein the powder is contained within a plastic housing designed for vaginal administration.

11. A method of preserving *Lactobacillus* spp. under dry conditions without animal-derived excipients, the method comprising:

(i) obtaining an aqueous suspension of vaginal *Lactobacillus* species having a cell concentration between $10^8$ to $10^{13}$ per ml;

(ii) centrifuging the solution to form a bacterial cell pellet; and (iii) resuspending the bacterial cell pellet in an aqueous preservation medium consisting of:

(a) trehalose at between 5-20%, w/v;

(b) xylitol at between 2-9%, w/v;

(c) sodium ascorbate 0.5-1.5%, w/v; and (d) sodium phosphate at between 10-50 mM;

where the weight ratio of cell pellet wet weight (grams) to preservation media (mL) is between 1:1 and 1:5 grams of cell pellet to milliliter of preservation media to yield a bacterial suspension.

12. The method of claim 11, wherein the bacterial suspension is lyophilized to yield a dry powder.

13. A method of treating abnormal vaginal microbiota in a woman comprising the steps of:

(i) selecting a woman having a diagnosis of abnormal vaginal microbiota;

(ii) administering to the woman an antibiotic in an amount effective to reduce the level of abnormal vaginal microbiota;

(iii) following step (ii), administering to the woman by vaginal administration the dry powder of claim 5.

14. The method of claim 13, wherein step (ii) includes daily administration of antibiotic for between 2 and 7 days and wherein step (iii) begins at any time between two days before the completion of antibiotic administration and two days after the administration of antibiotic in step (ii) ends.

15. The method of claim 13, wherein the vaginal *Lactobacillus* species is selected from the group consisting of *Lactobacillus crispatus, Lactobacillus jensenii*, and *Lactobacillus gasseri.*

16. The method of claim 13, wherein the dry powder is combined with an inactive excipient at a ratio of powder:excipient of between 1:1 and 1:10 w/w.

17. The method of claim 16, wherein the excipient is maltodextrin.

18. The method of claim 13, wherein the antibiotic is clindamycin, metronidazole, or tinidazole.

* * * * *